United States Patent
Kim et al.

(10) Patent No.: US 10,800,900 B2
(45) Date of Patent: *Oct. 13, 2020

(54) PLASTICIZER COMPOSITION, RESIN COMPOSITION AND METHOD FOR PREPARING THEREOF

(71) Applicant: LG CHEM, LTD., Seoul (KR)

(72) Inventors: Hyun Kyu Kim, Daejeon (KR); Mi Yeon Lee, Daejeon (KR); Jeong Ju Moon, Daejeon (KR); Joo Ho Kim, Daejeon (KR); Seok Ho Jeong, Daejeon (KR)

(73) Assignee: LG CHEM, LTD., Seoul (KR)

( * ) Notice: Subject to any disclaimer, the term of this patent is extended or adjusted under 35 U.S.C. 154(b) by 348 days.

This patent is subject to a terminal disclaimer.

(21) Appl. No.: 15/533,263

(22) PCT Filed: Apr. 6, 2016

(86) PCT No.: PCT/KR2016/003580
§ 371 (c)(1),
(2) Date: Jun. 5, 2017

(87) PCT Pub. No.: WO2016/163743
PCT Pub. Date: Oct. 13, 2016

(65) Prior Publication Data
US 2019/0211182 A1    Jul. 11, 2019

(30) Foreign Application Priority Data

Apr. 6, 2015 (KR) .................. 10-2015-0048543
Mar. 31, 2016 (KR) .................. 10-2016-0039670

(51) Int. Cl.
| | |
|---|---|
| *C08K 5/12* | (2006.01) |
| *C08K 5/00* | (2006.01) |
| *C07C 69/80* | (2006.01) |
| *C08L 101/00* | (2006.01) |
| *C08K 5/1535* | (2006.01) |
| *C08K 5/09* | (2006.01) |
| *C08K 5/11* | (2006.01) |
| *C08K 5/1515* | (2006.01) |
| *C08L 23/06* | (2006.01) |
| *C08L 23/08* | (2006.01) |
| *C08L 23/12* | (2006.01) |
| *C08L 25/06* | (2006.01) |
| *C08L 27/06* | (2006.01) |
| *C08L 75/04* | (2006.01) |

(52) U.S. Cl.
CPC ............ *C08K 5/0016* (2013.01); *C07C 69/80* (2013.01); *C08K 5/09* (2013.01); *C08K 5/11* (2013.01); *C08K 5/12* (2013.01); *C08K 5/1515* (2013.01); *C08K 5/1535* (2013.01); *C08L 23/06* (2013.01); *C08L 23/0853* (2013.01); *C08L 23/12* (2013.01); *C08L 25/06* (2013.01); *C08L 27/06* (2013.01); *C08L 75/04* (2013.01); *C08L 101/00* (2013.01); *C08L 2203/16* (2013.01); *C08L 2203/202* (2013.01)

(58) Field of Classification Search
CPC .............. C08K 5/00; C08K 5/016; C08K 5/04
USPC ........................................... 524/322
See application file for complete search history.

(56) References Cited

U.S. PATENT DOCUMENTS

| | | | |
|---|---|---|---|
| 3,926,889 A * | 12/1975 | Duchesneau, Jr. | C08J 3/18 523/300 |
| 5,319,028 A | 6/1994 | Nakamura et al. | |
| 2005/0020718 A1* | 1/2005 | Gosse | C08K 5/12 523/105 |
| 2008/0234414 A1* | 9/2008 | Godwin | C08K 5/101 524/112 |
| 2014/0315021 A1 | 10/2014 | Naert et al. | |
| 2016/0272780 A1 | 9/2016 | Kim et al. | |
| 2016/0376219 A1 | 12/2016 | Kim et al. | |

FOREIGN PATENT DOCUMENTS

| | | |
|---|---|---|
| CN | 102995451 B1 | 3/2013 |
| CN | 103012916 A | 4/2013 |
| CN | 103848595 A | 6/2014 |
| EP | 2927210 A1 | 10/2015 |
| GB | 851753 A | 10/1960 |
| JP | 2012-089287 A | 5/2012 |
| JP | 2012-255104 A | 12/2012 |
| KR | 10-1458311 B | 11/2014 |
| WO | 2012/169081 A1 | 12/2012 |

OTHER PUBLICATIONS

Derwent English abstract WO 2012169081 A1, published Dec. 2012 to Sakai (Year: 2012).*
Machine translation, WIPO, WO 2012169081 A1, published Dec. 2012 to Sakai (Year: 2012).*

* cited by examiner

*Primary Examiner* — Jane L Stanley
(74) *Attorney, Agent, or Firm* — Dentons US LLP

(57) ABSTRACT

The present invention relates to a plasticizer composition, a resin composition and a method for preparing thereof. The present invention can provide a plasticizer composition, which can improve properties required to the plasticizer composition contained in a vinyl chloride-based resin composition, such as plasticizing efficiency, tensile retention and elongation retention, volatile loss, and migration resistance, to a level equal to or better than the existing plasticizer composition, and a resin composition comprising thereof.

12 Claims, No Drawings

PLASTICIZER COMPOSITION, RESIN COMPOSITION AND METHOD FOR PREPARING THEREOF

CROSS-REFERENCE(S) TO RELATED APPLICATION

This application is a National Stage Entry of International Application No. PCT/KR2016/003580, filed on Apr. 6, 2016, and claims the benefit of Korean Application No. 10-2015-0048543, filed on Apr. 6, 2015, and Korean Patent Application No. 10-2016-0039670, filed on Mar. 31, 2016, all of which are hereby incorporated by reference in their entirety for all purposes as if fully set forth herein.

TECHNICAL FIELD

Field of the Invention

The present invention relates to a plasticizer composition, a method for preparing thereof and a resin composition comprising the same.

Background Art

In general, a plasticizer is composed of ester formed by reaction of alcohol with polycarboxylic acid such as phthalic acid and adipic acid. Further, in consideration of domestic and foreign regulations of harmful phthalate-based plasticizers, studies for a plasticizer composition, which can replace the phthalate-based plasticizer such as terephthalate-based, adipate-based, and other polymer-based plasticizer, are going on.

Meanwhile, in a compound business requiring high heat resistance and low volatile loss as a major property, it is needed to use a proper plasticizer in consideration of the required property. In the case of a PCV compound for a wire and a cable, additives such as a plasticizer, a stabilizer, a pigment and the like are mixed to PVC resin according to characteristics required in corresponding standards such as tensile strength, elongation rate, plasticizing efficiency, volatile loss, tensile retention and elongation retention.

Currently, diisodecyl phthalate (DIDP) representatively used for a wire compound, a vehicle fabric and the like is an endocrine disruptor observation material, and its use is regulated depending on environment issues. Thus, request of development of environment-friendly products, which can replace the DIDP, is rising, and development of new products having quality equal to or better than the DIDP thereby replacing the DIDP is needed.

Accordingly, studies for securing a vinyl chloride-based resin composition, which is free from environmental problems and has excellent quality by developing a new environment-friendly plasticizer composition product having better properties than the diisodecyl phthalate (DIDP), are going on.

DETAILED DESCRIPTION OF THE INVENTION

Technical Problem

Accordingly, the present inventors had been continuing research on a plasticizer, and completed the present invention after finding a plasticizer composition, which can improve properties of the vinyl chloride-based resin composition.

Namely, in order to solve the above problems, one object of the present invention is to provide a plasticizer composition, which can improve properties such as hardness, tensile retention and elongation retention, migration resistance and volatile loss when the composition is used as a plasticizer of a resin composition, a method for preparing thereof, and a resin composition comprising the same.

Technical Solution

In order to accomplish the objects described above, according to one embodiment of the present invention, provided is a plasticizer composition comprising an isophthalate-based compound; and epoxidized oil, wherein weight ratio of the isophthalate-based compound and the epoxidized oil is 99:1 to 1:99.

The isophthalate-based compound may comprise diisononyl isophthalate (DINIP).

The weight ratio of the isophthalate-based compound and the epoxidized oil may be 90:10 to 20:80.

The weight ratio of the isophthalate-based compound and the epoxidized oil may be 90:10 to 30:70, or 90:10 to 40:60.

The epoxidized oil may comprise at least one selected from the group consisting of epoxidized soybean oil, epoxidized castor oil, epoxidized linseed oil, epoxidized palm oil, epoxidized stearic acid, epoxidized oleic acid, epoxidized tall oil and epoxidized linoleic acid.

The epoxidized oil may be at least one selected from the group consisting of epoxidized soybean oil (ESO) and epoxidized linseed oil (ELO).

The plasticizer composition may further comprise an additive, wherein the additive is contained in an amount of 1 part by weight to 100 parts by weight, based on 100 parts by weight of a mixture of the isophthalate-based compound and the epoxidized oil.

The additive may comprise at least one compound selected from the group consisting of a phthalate-based compound, an acetyl citrate-based compound and a trimellitate-based compound.

The additive may comprise at least one selected from the group consisting of di-2-propylheptyl phthalate, diisodecyl phthalate, diisononyl phthalate, acetyl tributyl citrate (ATBC), acetyl triisobutyl citrate (ATiBC), acetyl triethylhexyl citrate (ATEHC), acetyl triisononyl citrate (ATiNC), triisobutyl trimellitate (TiBTM), tri-n-butyl trimellitate (Tn-BTM), triethylhexyl trimellitate (TEHTM) and triisononyl trimellitate (TINTM).

In order to accomplish the objects described above, according to another embodiment of the present invention, provided is a method for preparing the plasticizer composition, which comprises: a step of preparing the isophthalate-based compound and the epoxidized oil; and a step of obtaining the plasticizer composition by blending the isophthalate-based compound and the epoxidized oil at weigh ratio of 99:1 to 1:99.

The method may further comprise a step of mixing the additive in an amount of 1 part by weight to 100 parts by weight, based on 100 parts by weight of the plasticizer composition, after the step of obtaining the plasticizer composition by blending.

The additive may comprise at least one compound selected from the group consisting of a phthalate-based compound, an acetyl citrate-based compound and a trimellitate-based compound.

In order to accomplish the objects described above, according to further another embodiment of the present invention, provided is a resin composition comprising resin 100 parts by weight; and the plasticizer composition described above 5 parts by weight to 150 parts by weight.

The resin may be at least one selected from the group consisting of ethylene vinyl acetate, polyethylene, polypropylene, polyvinyl chloride, polystyrene, polyurethane and thermoplastic elastomer.

The resin composition may be applied for manufacturing at least one selected from the group consisting of a wire, a flooring material, an interior material for a vehicle, a film, a sheet, wallpaper and a tube.

Advantageous Effect

The plasticizer composition according to one embodiment of the present invention can enhance properties such as plasticizing efficiency, tensile strength and elongation rate, and also can provide excellent properties in items such as migration resistance and volatile loss when used for a resin composition.

BEST MODE FOR CARRYING OUT THE INVENTION

Example

Hereinafter, the preferred embodiment of the present invention will be described in detail based on examples. However, the embodiments of the present invention may be modified in various ways, and the scope of the present invention should not be interpreted as being limited to the examples. The embodiments of the present invention are provided just for explaining the present invention more perfectly to those having ordinary skill in the art.

Preparation Example 1: Preparation of Diisononyl Isophthalate (DINIP)

Purified isophthalic acid (PIA) 498.0 g and isononyl alcohol (INA) 1298.3 g (molar ratio of PIA and INA was 1.0:3.0), and a titanium catalyst (tetra isopropyl titanate (TIPT)) as a catalyst 1.54 g (0.31 part by weight, based on PIA 100 parts by weight) were put into a 4-neck 3-liter reactor equipped with a cooler, a water stripper, a condenser, a decanter, a reflux pump, a temperature controller, a stirrer and the like, and then slowly heated up to about 170° C. Product water begun to be formed around 170° C. Esterification reaction was conducted for about 4.5 hour at a reaction temperature of about 220° C. under atmospheric pressure while continuously inserting nitrogen gas, and the reaction was completed when acid value reached 0.01.

After the reaction was completed, distillation extraction was conducted for 0.5 hour to 4 hours under reduced pressure to remove unreacted raw materials. In order to remove the unreacted raw materials below a certain content level, steam extraction was conducted using steam for 0.5 hour to 3 hours under reduced pressure, and the reacted solution was cooled to a temperature of about 90° C. and then neutralized using alkali solution. In addition, washing may be conducted, and then the reacted solution was dehydrated to remove moisture. Media were inserted to the dehydrated reacted solution followed by stirring thereof for a period of time, and then the solution was filtered to finally obtain diisononyl isophthalate 1243.3 g (Yield: 99.0%).

Plasticizer compositions of Examples 1 and 2 were prepared using the diisononyl isophthalate prepared in the above Preparation Example 1, epoxidized oil and the like as shown in the following Tables 1 and 2, and evaluation of properties of the plasticizer compositions were conducted according to the following test items.

TABLE 1

| | Terephthalate-based material | Epoxidized oil | Weight ratio for mixing |
|---|---|---|---|
| Example 1-1 | Preparation Example 1 (DINIP) | ESO | 5:5 |
| Example 1-2 | | | 7:3 |
| Example 1-3 | | | 9:1 |
| Example 1-4 | | ELO | 3:7 |
| Example 1-5 | | ESO | 1:9 |

TABLE 2

| | Terephthalate-based material | Epoxidized oil | Additives | Weight ratio for mixing |
|---|---|---|---|---|
| Example 2-1 | Preparation Example 1 (DINIP) | ESO | DPHP | 4:3:3 (about 43 parts) |
| Example 2-2 | | | DPHP | 4:2:4 (about 66 parts) |
| Example 2-3 | | | DPHP | 3:2:5 (about 100 parts) |
| Example 2-4 | | | ATOC | 6:2:2 (about 25 parts) |
| Example 2-5 | | | ATOC | 4:2:4 (about 66 parts) |
| Example 2-6 | | | TBTM | 5:2:3 (about 43 parts) |
| Comparative Example 2-1 | | | DPHP | 2:2:6 (about 150 parts) |
| Comparative Example 2-2 | | | ATOC | 2:2:6 (about 150 parts) |

<Property Test Item>

Measuring Hardness

Using ASTM D2240, shore hardness at 25° C., 3T 10s was measured.

Measuring Tensile Strength

According to ASTM D638 method, a test specimen was pulled using a tester U.T.M (Manufacturer; Instron, Model No.; 4466) at cross head speed of 200 mm/min (1T), and then a point when the test specimen was broken was measured. Tensile strength was calculated as follows:

Tensile Strength (kgf/cm$^2$)=Load value (kgf)/Thickness (cm)×Width (cm)

Tensile Retention

The method for measuring tensile strength as described above was repeated except for using a test specimen exposed at 121° C. for 168 hours.

Measuring Elongation Rate

According to ASTM D638 method, a test specimen was pulled using a tester U.T.M at cross head speed of 200 mm/min (1T), and then a point when the test specimen was broken was measured. Elongation rate was calculated as follows:

Elongation Rate (%)=Length after elongation/Initial length×100

Elongation Retention

The method for measuring elongation rate as described above was repeated except for using a test specimen exposed at 121° C. for 168 hours.

Measuring Migration Loss

A test specimen having thickness of 2 mm or thicker was obtained according to KSM-3156, and PS Plates were attached to both sides of the test specimen followed by adding a load of 1 kgf/cm² thereto. The test specimen was left in a hot air circulation oven (80° C.) for 72 hours, taken out therefrom, and then cooled at an ordinary temperature for 4 hours. Then, the PS plates attached to both sides of the test specimen were removed, weight before and after left in the oven was measured, and then migration loss was calculated according to the following formula.

Migration Loss (%)={(Initial weight of test specimen at ordinary temperature−Weight of test specimen after left in oven)/Initial weight of test specimen at ordinary temperature}×100

Measuring Volatile Loss

The prepared test specimen was processed for at 100° C. for 168 hours, weight of the test specimen was measured, and then volatile loss was calculated according to the following formula.

Volatile Loss (wt %)=Initial weight of test specimen−(Weight of test specimen after processed at 100° C. for 168 hours)/Initial weight of test specimen×100

Measuring Heat Resistance

According to a method for measuring volatile loss, degree of discoloration of an initial test specimen and a test specimen after volatile loss test was measured. The measured value was determined by difference in E value against L, a and b values obtained by using a colorimeter.

Test Example 1: DINIP and Epoxidized Oil-Mixed Plasticizer Composition

Evaluation of Basic Property

Referring to ASTM D638, test specimens were manufactured from the plasticizer compositions of Examples 1-1 to 1-5 and Comparative Example 1 according to the following method.

Based on polyvinyl chloride resin (PVC(LS100)) 100 parts by weight, the plasticizer compositions prepared in Examples and Comparative Example 50 parts by weight, and RUP 144 (Adeka Korea) 5 parts by weight, Omya 1T (Omya) 40 parts by weight and St-A (Isu Chemical) 0.3 phr as additives were mixed and blended at 1300 rpm and 100° C. The mixture was processed using a roll mill at 175° C. for 4 min, and then processed using a press at 185° C. for 3 min (low pressure) and 2 min 30 sec (high pressure) to obtain a 2 mm-thick test specimen.

The results of evaluating performance of each test specimen against the above items were shown in the following Table 3.

As shown in the above Table 3, compared to the compound of Comparative Example 1 using DIDP plasticizer that is a product broadly sold already in the market, it can be found that the compound of Example 1-1 has properties similar to or better than the compound of Comparative Example 1. In other words, it can be found that the resin composition using the plasticizer composition, which is a mixture of the DINIP of the present invention and epoxidized oil, can replace the DIDP whose use was restricted and regulated due to environmental problems, and can be used for manufacturing a compound, which can provide better properties than the DIDP.

Like this, it can be found that the plasticizer composition of the present invention has enhanced plasticizing efficiency, tensile strength and elongation rate, compared to the existing products, and in particular, the composition has improved major properties such as migration loss, tensile retention and elongation retention, and volatile loss by extraordinary reduction of the properties.

Through this, it can be confirmed that, compared to the existing phthalate plasticizer products, the mixed plasticizer composition of the present invention has better influence on the property enhancement of a product.

Stress Test

Test specimens were manufactured from the plasticizer compositions of Examples 1-1 to 1-5 and Comparative Example 1 according to the same method of Test Example 1. The manufactured test specimens were subjected to a stress test.

For the stress test, the test specimen was kept bending at an ordinary temperature for 24 hours, and then degree of migration and modification (degree of escaping) was observed. Each test specimen was subjected to the following property tests, and the results were shown in the following Table 4. As the value stated in evaluation section of the following Table 4 is closer to 0, the value means better characteristic.

TABLE 4

|  | Plasticizer | Evaluation |
| --- | --- | --- |
| Example 1-1 | DINIP + ESO (5:5) | 0.5 |
| Example 1-2 | DINIP + ESO (7:3) | 0.5 |
| Example 1-3 | DINIP + ESO (9:1) | 1.5 |
| Example 1-4 | DINIP + ELO (3:7) | 0 |
| Example 1-5 | DINIP + ESO (1:9) | 0 |
| Comparative Example 1 | DIDP | 0.5 |

TABLE 3

|  | Plasticizer | Hardness (Shore "A") | Tensile Strength (kg/cm²) | Tensile Retention (%) | Elongation Rate (%) | Elongation Retention (%) | Migration Loss (%) | Volatile Loss (%) | Heat Resistance (E) |
| --- | --- | --- | --- | --- | --- | --- | --- | --- | --- |
| Example 1-1 | DINIP + ESO (5:5) | 87.0 | 176.5 | 110.1 | 311.1 | 98.9 | 0.01 | 0.12 | 12.36 |
| Example 1-2 | DINIP + ESO (7:3) | 88.5 | 182.5 | 101.1 | 318.0 | 101.3 | 0.02 | 0.33 | 9.78 |
| Example 1-3 | DINIP + ESO (9:1) | 89.5 | 183.3 | 101.6 | 316.5 | 104.0 | 0.03 | 0.48 | 8.99 |
| Example 1-4 | DINIP + ELO (3:7) | 86.5 | 173.2 | 112.5 | 310.5 | 101.3 | 0.01 | 0.25 | 10.58 |
| Example 1-5 | DINIP + ESO (1:9) | 86.1 | 170.5 | 115.3 | 308.7 | 100.2 | 0.01 | 0.05 | 10.95 |
| Comparative Example 1 | DIDP | 90.3 | 167.9 | 102.5 | 282.3 | 92.5 | 0.16 | 1.10 | 10.65 |

Referring to Table 4, except for Example 1-3, Examples 1-1, 1-2, 1-4 and 1-5 and the existing product (Comparative Example 1) showed good results. The case of increasing weight ratio of the epoxidized oil like Examples 1-4 and 1-5 showed better properties than the existing product, and the case of containing relatively small amount of the epoxidized oil like Examples 1-1 and 1-2 showed properties of equivalent level.

In other words, it can be found that the case of mixing the isophthalate-based compound and the epoxidized oil can secure stress resistance characteristic equal to or better than the existing plasticizer composition.

Test Example 2: DINIP, Epoxidized Oil and Additives-Mixed Plasticizer Composition Referring to ASTM D638, test specimens were manufactured from the plasticizer compositions of Examples 2-1 to 2-6 according to the same method of Test Example 1, and properties thereof were evaluated on the basis of the above evaluation items. The results were shown in the following Table 5.

TABLE 5

| | Plasticizer | Hardness (Shore "A") | Tensile Strength (kg/cm$^2$) | Tensile Retention (%) | Elongation Rate (%) | Elongation Retention (%) | Migration Loss (%) | Volatile Loss (%) | Heat Resistance (E) |
|---|---|---|---|---|---|---|---|---|---|
| Example 2-1 | DPHP (about 43 parts) | 89.5 | 178.5 | 106.4 | 302.5 | 93.5 | 0.14 | 0.56 | 9.86 |
| Example 2-2 | DPHP (about 66 parts) | 89.8 | 181.2 | 104.5 | 305.8 | 94.8 | 0.13 | 0.68 | 8.23 |
| Example 2-3 | DPHP (about 100 parts) | 90.4 | 185.6 | 104.0 | 311.5 | 98.2 | 0.12 | 1.12 | 8.01 |
| Example 2-4 | TOC (about 25 parts) | 88.7 | 172.3 | 103.5 | 308.6 | 95.6 | 0.10 | 0.51 | 7.81 |
| Example 2-5 | TOC (about 66 parts) | 89.8 | 175.9 | 101.8 | 312.5 | 97.8 | 0.06 | 0.26 | 5.68 |
| Example 2-6 | TBTM (about 43 parts) | 88.3 | 171.8 | 101.2 | 322.1 | 101.5 | 0.15 | 1.11 | 8.54 |
| Comparative Example 1 | DIDP | 90.3 | 167.9 | 102.5 | 282.3 | 92.5 | 0.16 | 1.10 | 10.65 |
| Comparative Example 2-1 | DPHP (about 150 parts) | 91.2 | 162.4 | 89.5 | 275.1 | 86.5 | 0.10 | 1.45 | 9.55 |
| Comparative Example 2-2 | TOC (about 150 parts) | 91.8 | 158.7 | 82.6 | 271.2 | 85.7 | 0.08 | 0.19 | 10.21 |

As shown in Table 5, it can be confirmed that the cases of Examples 2-1 to 2-6 manufacturing the plasticizer compositions by mixing the epoxidized oil with the DINIP, and additionally adding the DPHP, the ATOC, the TBTM and the like as additives by content showed properties such as tensile strength, volatile loss, migration loss, elongation rate and the like equal to or better than the existing DIDP plasticizer of Comparative Example 1.

Further, considering that although the mixed plasticizer compositions contained the epoxidized oil in an amount of 20 wt % or more, the properties such as hardness or tensile strength were better than those of the existing plasticizer, DIDP, it can be indirectly confirmed that the effect is improved by the additives, and also it can be confirmed that if the amount of the additives is excessive, the properties such as plasticizing efficiency, tensile strength and tensile retention, and elongation rate and elongation retention may be rather deteriorated, compared to Comparative Example 2-1 and Comparative Example 2-2 containing the additives in an amount of more than 100 parts by weight.

It can be confirmed that the existing DIDP plasticizer had excellent properties but its use was regulated due to environmental problems, but it can provide a plasticizer composition, which can replace the DIDP plasticizer in businesses such as compound, by additionally adding the acetyl citrate-based material, the trimellitate-based material or the phthalate-based material as described above.

While the invention has been shown and described with reference to exemplary embodiments thereof, it will be understood by those skilled in the art that various changes in form and details may be made therein without departing from the spirit and scope of the invention as defined by the appended claims. Therefore, the scope of the invention is defined not by the detailed description of the invention but by the appended claims, and all differences within the scope will be construed as being included in the present invention.

MODE FOR THE INVENTION

Hereinafter, the present invention will be described in more detail.

According to one embodiment of the present invention, a plasticizer composition containing an isophthalate-based compound can be provided. Specifically, the content of the isophthalate-based compound may be selected from the range of 1 wt % to 99 wt %, 10 wt % to 99 wt %, 20 wt % to 99 wt %, 30 wt % to 95 wt %, 40 wt % to 90 wt % and the like, based on the total weight of the composition. Further, the content may be selected from the range of 1 wt % to 50 wt %, 10 wt % to 50 wt %, 10 wt % to 40 wt %, 25 wt % to 50 wt %, 25 wt % to 40 wt % and the like.

Preferably, the isophthalate-based compound may be diisononyl isophthalate (DINIP). If the diisononyl isophthalate is used as the isophthalate-based compound, the compound can be freer from environmental problems than a phthalate-based compound, and can secure properties equal to or better than the existing products.

According to one embodiment of the present invention, the plasticizer composition comprises the isophthalate-based compound, and further comprises epoxidized oil. Like this, in the case of a resin manufactured from the plasticizer composition wherein the isophthalate-based compound and the epoxidized oil are mixed together, the resin may have better properties such as tensile strength or elongation rate than a resin manufactured from the plasticizer composition comprising only the isophthalate-based compound, and also have better tensile retention and elongation retention, volatile loss, and migration resistance.

Herein, the isophthalate-based compound and the epoxidized oil in the plasticizer composition may be contained at weight ratio of 1:99 to 99:1.

If the isophthalate-based compound is the diisononyl isophthalate, for example, the weight ratio may be 99:1 to 1:99, 90:10 to 10:90, 90:10 to 30:70, or 90:10 to 20:80, and preferably, the weight ratio may be 90:10 to 40:60. In the case of increasing the addition amount of the epoxidized oil, migration resistance characteristic against stress may become excellent, but properties such as tensile strength or elongation rate may be a little deteriorated within the required property range. Thus, according to control of the epoxidized oil content, the required property can be freely controlled, thereby properly applying the property depending on purpose of a vinyl chloride-based resin composition.

The epoxidized oil may be, for example, epoxidized soybean oil, epoxidized castor oil, epoxidized linseed oil, epoxidized palm oil, epoxidized stearic acid, epoxidized oleic acid, epoxidized tall oil, epoxidized linoleic acid or a mixture thereof.

Preferably, the epoxidized oil may be the epoxidized soybean oil (ESO), the epoxidized linseed oil (ELO) or a mixture thereof, but the epoxidized soybean oil may be more frequently used than the epoxidized linseed oil due to market conditions, supply and demand problems and the like.

The plasticizer composition may further comprise additives, and the additives may be contained in an amount of 1 part by weight to 100 parts by weight, preferably, 10 parts by weight to 80 parts by weight, based on 100 parts by weight of the mixture of the isophthalate-based compound and the epoxidized oil. The additives can enhance properties of the resin composition such as stress characteristic by being mixed with only the isophthalate-based compound, but as mentioned above, a compound and the like having excellent properties can be manufactured by mixing only a small amount of the additives to the plasticizer composition. If a larger amount of the additives is contained, there may be problems that controlling the properties of the plasticizer composition suitable for purpose may be out of scope of control, undesired properties may be excessively improved, or desired properties may be deteriorated.

The additives may be at least one compound selected from the group consisting of phthalate-based compound, acetyl citrate-based compound and trimellitate-based compound.

The phthalate-based compound may be, for example, di-2-propylheptyl phthalate, diisodecyl phthalate or diisononyl phthalate, and the acetyl citrate-based compound may be various acetyl citrate-based compounds, for example, acetyl tributyl citrate (ATBC), acetyl triisobutyl citrate (TiBC), acetyl triethylhexyl citrate (ATEHC), acetyl triisononyl citrate (ATiNC) and the like. Further, the trimellitate-based compound also may be used in various forms similar with the acetyl citrate-based compound, for example, triisobutyl trimellitate (TiBTM), tri-n-butyl trimellitate (Tn-BTM), triethylhexyl trimellitate (TEHTM), triisononyl trimellitate (TINTM) and the like.

As described above, if the phthalate-based compound, the acetyl citrate-based compound or the trimellitate-based compound is used as the additives, plasticizing efficiency, tensile strength, elongation rate and the like can be improved depending on a material to be mixed with, and additional effects, for example, improvement of stress migration characteristic, migration resistance and the like can be obtained.

In the present invention, a method for preparing the plasticizer composition may be a blending method, and for example, the blending method is as follows:

The isophthalate-based compound and the epoxidized oil are prepared.

The isophthalate-based compound and the epoxidized oil are blended at weight ratio of 99:1 to 1:99 to manufacture the plasticizer composition.

In the above blending method, the isophthalate-based compound can be prepared by direct esterification reaction comprising: a step of inserting isophthalic acid to alcohol, adding a catalyst thereto, and then reacting thereof under nitrogen atmosphere; a step of removing unreacted alcohol and then neutralizing unreacted acid; and a step of dehydrating thereof by distillation under reduced pressure and then filtering thereof.

Further, the alcohol used in the blending method may be, for example, isononyl alcohol and the like and used in an amount within the range of 150 mol % to 500 mol %, 200 mol % to 400 mol %, 200 mol % to 350 mol %, 250 mol % to 400 mol %, or 270 mol % to 330 mol %, based on the isophthalic acid 100 mol %.

On the other hand, the catalyst used in the blending method may be any catalyst, which can be used in esterification reaction without particular limitation, and for example, it may be at least one selected from the group consisting of acid catalysts such as sulfuric acid, hydrochloric acid, phosphoric acid, nitric acid, paratoluenesulfonic acid, methanesulfonic acid, ethanesulfonic acid, propanesulfonic acid, butanesulfonic acid and alkyl sulfuric acid; metal salts such as aluminum lactate, lithium fluoride, potassium chloride, cesium chloride, calcium chloride, iron chloride and aluminum phosphate; metal oxides such as heteropolyacids; and organic metal such as natural/synthetic zeolite, cation and anion exchange resins, tetra alkyl titanate and its polymer. Specifically, the catalyst may be tetra alkyl titanate.

Amount of the catalyst may vary depending on its kind, and for example, a homogeneous catalyst may be used in an amount within the range of 0.01 wt % to 5 wt %, 0.01 wt % to 3 wt %, 1 wt % to 5 wt % or 2 wt % to 4 wt %, based on total reactant 100 wt %, and a heterogeneous catalyst may be used in an amount within the range of 5 wt % to 200 wt %, 5 wt % to 100 wt %, 20 wt % to 200 wt %, or 20 wt % to 150 wt %, based on total reactant.

At this time, a reaction temperature may be within the range of 180° C. to 280° C., 200° C. to 250° C., or 210° C. to 230° C.

The plasticizer composition manufactured as described above may be used in an amount within the range of 5 parts by weight to 150 parts by weight, 40 parts by weight to 100 parts by weight, or 40 parts by weight to 50 parts by weight, based on 100 parts by weight of a resin such as ethylene vinyl acetate, polyethylene, polypropylene, polyvinyl chloride, polystyrene, polyurethane, thermoplastic elastomer, or a mixture thereof, and also can provide a resin composition effective on compound formulation and/or sheet formulation.

According to one embodiment of the present invention, the resin composition may further comprise a filler.

The filler may be contained in an amount of 0 part by weight to 300 parts by weight, preferably, 50 parts by weight to 200 parts by weight, more preferably, 100 parts by weight to 200 parts by weight, based on the resin 100 parts by weight.

According to one embodiment of the present invention, the filler may be a filler known in the art without particular limitation. For example, the filler may be a mixture of at least one selected from the group consisting of silica, magnesium carbonate, calcium carbonate, precipitated calcium carbonate, talc, magnesium hydroxide, titanium dioxide, magnesium oxide, calcium hydroxide, aluminum hydroxide, aluminum silicate, magnesium silicate and barium sulfate.

Further, according to one embodiment of the present invention, the resin composition may further comprise other additives such as a stabilizer and the like as occasion demands.

The other additives such as a stabilizer and the like may be contained in an amount of, for example, 0 part by weight to 20 parts by weight, preferably, 1 part by weight to 15 parts by weight, based on the resin 100 parts by weight.

The stabilizer, which can be used according to one embodiment of the present invention, may be, for example, a calcium-zinc-based (Ca—Zn-based) stabilizer such as a complex stearate salt of calcium-zinc and the like, but not particularly limited thereto.

The resin composition can be applied to various fields, but as non-restrictive examples, it can be applied for manufacturing a wire, a flooring material, an interior material for a vehicle, a film, a sheet, wallpaper or a tube and the like.

The invention claimed is:

1. A plasticizer composition comprising diisononyl isophthalate (DINIP) and an epoxidized oil,
   wherein a weight ratio of the diisononyl isophthalate and the epoxidized oil is 90:10 to 50:50.

2. The plasticizer composition of claim 1, wherein the epoxidized oil comprises at least one selected from the group consisting of epoxidized soybean oil, epoxidized castor oil, epoxidized linseed oil, epoxidized palm oil, epoxidized stearic acid, epoxidized oleic acid, epoxidized tall oil and epoxidized linoleic acid.

3. The plasticizer composition of claim 2, wherein the epoxidized oil is at least one selected from the group consisting of epoxidized soybean oil (ESO) and epoxidized linseed oil (ELO).

4. The plasticizer composition of claim 1, wherein the plasticizer composition further comprises an additive,
   wherein the additive is contained in an amount of 1 part by weight to 100 parts by weight, based on 100 parts by weight of a mixture of the diisononyl isophthalate and the epoxidized oil.

5. The plasticizer composition of claim 4, wherein the additive comprises at least one compound selected from the group consisting of a phthalate-based compound, an acetyl citrate-based compound and a trimellitate-based compound.

6. The plasticizer composition of claim 1, wherein the additive comprises at least one selected from the group consisting of di-2-propylheptyl phthalate, diisodecyl phthalate, diisononyl phthalate, acetyl tributyl citrate (ATBC), acetyl triisobutyl citrate (ATiBC), acetyl triethylhexyl citrate (ATEHC), acetyl triisononyl citrate (ATiNC), triisobutyl trimellitate (TiBTM), tri-n-butyl trimellitate (TnBTM), triethylhexyl trimellitate (TEHTM) and triisononyl trimellitate (TINTM).

7. A resin composition comprising 100 parts by weight of a the resin and 5 parts by weight to 150 parts by weight of the plasticizer composition of claim 1.

8. The resin composition of claim 7, wherein the resin is at least one selected from the group consisting of ethylene vinyl acetate, polyethylene, polypropylene, polyvinyl chloride, polystyrene, polyurethane and thermoplastic elastomer.

9. The resin composition of claim 7, which is applied to manufacturing at least one selected from the group consisting of a wire, a flooring material, an interior material for a vehicle, a film, a sheet, wallpaper and a tube.

10. A method for preparing a plasticizer composition, which comprises:
    a step of selecting diisononyl isophthalate and an epoxidized oil; and
    a step of preparing a plasticizer composition by blending the diisononyl isophthalate and the epoxidized oil at weigh ratio of 90:10 to 50:50.

11. The method for preparing a plasticizer composition of claim 10, which further comprises a step of mixing an additive in an amount of 1 part by weight to 100 parts by weight, based on 100 parts by weight of the mixture of the diisononyl isophthalate and the epoxidized oil, after the step of obtaining a plasticizer composition by blending.

12. The method for preparing a plasticizer composition of claim 11, wherein the additive comprises at least one compound selected from the group consisting of a phthalate-based compound, an acetyl citrate-based compound and a trimellitate-based compound.

* * * * *